United States Patent
Marissal et al.

(10) Patent No.: US 9,139,673 B2
(45) Date of Patent: Sep. 22, 2015

(54) PROCESS FOR INTRODUCTION OF LIQUID FEEDS TO A POLYMERIZATION PROCESS

(71) Applicant: Ineos Europe AG, Vaud (CH)

(72) Inventors: Daniel Marissal, Casteau (BE); Philip Van Breuseghem, Temse (BE); Brent R. Walworth, Sint-Niklaas (BE)

(73) Assignee: INEOS EUROPE AG, Vaud (CH)

( * ) Notice: Subject to any disclaimer, the term of this patent is extended or adjusted under 35 U.S.C. 154(b) by 0 days.

(21) Appl. No.: 14/382,147

(22) PCT Filed: Mar. 7, 2013

(86) PCT No.: PCT/EP2013/054649
§ 371 (c)(1),
(2) Date: Aug. 29, 2014

(87) PCT Pub. No.: WO2013/135564
PCT Pub. Date: Sep. 19, 2013

(65) Prior Publication Data
US 2015/0025202 A1 Jan. 22, 2015

(30) Foreign Application Priority Data

Mar. 16, 2012 (EP) .................................. 12159940
Mar. 16, 2012 (EP) .................................. 12159942
Mar. 16, 2012 (EP) .................................. 12159944

(51) Int. Cl.
*C08F 2/06* (2006.01)
*C08F 2/38* (2006.01)
*C08F 6/00* (2006.01)
*C08F 210/16* (2006.01)
*C08F 2/01* (2006.01)
*C07C 7/00* (2006.01)

(52) U.S. Cl.
CPC ................ *C08F 210/16* (2013.01); *C07C 7/00* (2013.01); *C08F 2/01* (2013.01); *C08F 2/06* (2013.01); *C08F 6/001* (2013.01)

(58) Field of Classification Search
USPC ...................................... 526/68, 77; 528/501
See application file for complete search history.

(56) References Cited

U.S. PATENT DOCUMENTS

| | | | |
|---|---|---|---|
| 3,152,872 | A | 10/1964 | Scoggin et al. |
| 3,842,060 | A | 10/1974 | McDonald et al. |
| 4,182,810 | A | 1/1980 | Willcox |
| 4,215,207 | A | 7/1980 | Durand et al. |
| 4,424,341 | A | 1/1984 | Hanson et al. |
| 4,589,957 | A | 5/1986 | Sherk et al. |
| 6,042,790 | A | 3/2000 | Hattovy et al. |
| 6,262,191 | B1 | 7/2001 | Hottovy et al. |
| 2003/0191251 | A1 | 10/2003 | McGrath |
| 2007/0142576 | A1 | 6/2007 | Tait et al. |

FOREIGN PATENT DOCUMENTS

| | | |
|---|---|---|
| EP | 2 336 200 A1 | 6/2011 |
| EP | 2 336 201 A1 | 6/2011 |
| WO | WO 94/28032 A1 | 12/1994 |
| WO | WO 99/60028 A2 | 11/1999 |
| WO | WO 00/42077 A1 | 7/2000 |
| WO | WO 00/53306 A1 | 9/2000 |
| WO | WO 2004/039847 A1 | 5/2004 |
| WO | WO 2005/003188 A1 | 1/2005 |
| WO | WO 2006/015807 A1 | 2/2006 |
| WO | WO 2009/070261 A2 | 6/2009 |
| WO | WO 2009/070261 A3 | 6/2009 |
| WO | WO 2009/070261 A8 | 6/2009 |
| WO | WO 2011/076371 A1 | 6/2011 |

OTHER PUBLICATIONS

Specification of Co-pending National Phase Application Serial No. 14/382,114, filed Aug. 29, 2014; PCT Int'l Application No. PCT/EP2013/054645, WO 2013/135563 A1, filed Sep. 19, 2013; 21 pgs.
Specification of Co-pending National Phase Application Serial No. 14/382,185, filed Aug. 29, 2014; PCT Int'l Application No. PCT/EP2013/054650, WO 2013/135565 A1, filed Mar. 7, 2013; 22 pgs.

*Primary Examiner* — Fred M Teskin
(74) *Attorney, Agent, or Firm* — Nixon & Vanderhye P.C.

(57) ABSTRACT

Process for the introduction of liquid feeds to a polymerization process, and in particular for the introduction of a fresh feed selected from fresh comonomer and fresh inert hydrocarbon to a polymerization reactor. The process includes passing the fresh feed and a process stream containing a first component selected from hydrogen, nitrogen and methane and a second component which is a monomer to a separator at a pressure of 0.4 MPa (4 bar) or less to produce a first stream containing the majority of the first component and a second stream containing the majority of the fresh feed and the majority of the second component, and passing the second stream to the polymerization reactor.

19 Claims, No Drawings

PROCESS FOR INTRODUCTION OF LIQUID FEEDS TO A POLYMERIZATION PROCESS

This application is the U.S. national phase of International Application No. PCT/EP2013/054649 filed Mar. 7, 2013 which designated the U.S. and claims priority to European Patent Application Nos. 12159940.1, filed Mar. 16, 2012, 12159942.7, filed Mar. 16, 2012, and 12159944.3, filed Mar. 16, 2012, the entire contents of each of which are hereby incorporated by reference.

BACKGROUND OF THE INVENTION

The present invention relates to a process for the introduction of liquid feeds to a polymerisation process.

The production of polymer powder by polymerisation reactions of monomers in the presence of catalysts is well-known. For example, processes are known and widely operated commercially using both fluidised bed reactors and slurry phase reactors.

In a slurry polymerisation process, for example, the polymerisation is conducted in a stirred tank or, preferably, a continuous loop reactor in which a slurry of polymer particles in a liquid medium comprising hydrocarbon diluent is circulated. During the course of polymerisation, fresh polymer is generated by the catalytic polymerisation of monomer and polymer product is removed from the reactor by removing a portion of the slurry.

The slurry withdrawn may be treated to separate the polymer particles from the hydrocarbon diluent and other components, such as unreacted monomers, which it is generally desired are recycled to the process.

A polymerisation process generally includes feed systems for fresh monomer and comonomer, as well as for fresh inert liquids. Fresh feeds of monomer and co-monomer for example are fed to the polymerisation process to replace monomer and comonomer consumed in the reaction. Although inert liquids don't react they can be lost from the system in purges or as residual amounts in the polymer passed to downstream storage and processing.

Thus, it is common to have fresh feeds for each of the process components. The fresh feeds are usually treated to remove components which may act as poisons in the polymerisation process, or which, even if not poisons, may otherwise build-up in the process and require larger purges to be taken. (Unless separation of the component is very efficient, any increase in purge rates is likely to lead to increased loss of useful materials as well.)

U.S. Pat. No. 6,051,631, for example, discloses a process to treat fluid streams to remove undesirable compounds, in particular to treat monomer, comonomer and diluent streams to a polymerisation process.

In general, treatment comprises passing the respective streams to a treatment bed, usually comprising a fixed bed of a suitable absorbent for the impurities it is desired to remove. Two or more treatment beds for a particular feed may be provided in parallel to allow one to be regenerated whilst another is in use, as described in U.S. Pat. No. 6,051,631. It is also possible that certain streams, such as diluent and comonomer, can be mixed and passed to a common treatment bed, such as also described in U.S. Pat. No. 6,051,631.

The treated streams are then passed to the reactor (or reactors where more than one are present).

SUMMARY OF THE INVENTION

We have now found that introduction of fresh liquids to a polymerisation process can advantageously be achieved by not passing said streams directly to the reactor but by instead passing them to a low pressure separator which is already present in the low pressure part of the recovery system of a polymerisation process.

Thus, in a first aspect, the present invention provides a process for the introduction of a fresh feed selected from fresh comonomer and fresh inert hydrocarbon to a polymerisation reactor, which process comprises passing said fresh feed and a process stream comprising a first component selected from hydrogen, nitrogen and methane and a second component which is a monomer to a separator at a pressure of 0.4 MPa (4 bar) or less to produce a first stream comprising the majority of the first component and a second stream comprising the majority of the fresh feed and the majority of the second component, and passing the second stream to the polymerisation reactor.

In this first aspect, the fresh feed is passed to a separation step at a pressure of 0.4 MPa (4 bar) or less with a process stream comprising the first and second components. This is preferably performed by mixing the fresh feed and process stream to form a mixed stream which is passed to the separator.

DETAILED DESCRIPTION OF THE INVENTION

The term "fresh" as used herein means a feed/component which is being passed to the reactor for the first time and can be contrasted with process streams which contain components recovered from the reactor effluent, usually for recycle. However, for avoidance of doubt "fresh" streams may have been subjected to pre-treatments to reduce impurities.

The term "process stream" as used herein means a stream which is present in the recycle and recovery system by which components which it is desired to recover from the reactor effluent are recycled to the reactor. The process stream comprises a first component selected from hydrogen, nitrogen and methane. Preferably the first component is nitrogen. However, more generally, hydrogen, nitrogen and methane may all be present in the process stream. The process stream comprises a second component which is a monomer.

The process stream will generally comprise a number of other components which are present in the polymerisation reactor. Thus, where a comonomer is fed to the process then the process stream generally also comprises comonomer. Other components which may be present include impurities associated with the main components in the reactor. For example alkanes such as ethane and propane may be present as impurities in ethylene feeds, and butane and hexane may be present as impurities in 1-butene and 1-hexene respectively.

The present invention is particularly applicable to the polymerisation of olefins in gas phase or slurry phase reactors.

The polymerisation reactor is preferably a slurry phase polymerisation reactor. The inert hydrocarbon is preferably iso-butane.

For avoidance of any doubt, where more than one olefin is present in the polymerisation reaction, the term "monomer" as used herein refers to the olefin which is present in the largest amount in the formed polymer, and may also be referred to as the "principal monomer".

The monomer is preferably ethylene or propylene, most preferably ethylene. The term "comonomer" as used herein refers to olefins other than the monomer which may be present. More than one comonomer may be present.

Where ethylene is the monomer, propylene may be the comonomer, but the comonomer is preferably selected from 1-butene, 1-hexene and 1-octene, with 1-hexene being most preferred.

Where propylene is the monomer, the comonomer is preferably selected from ethylene, 1-butene, 1-hexene and 1-octene.

The comonomer is preferably 1-hexene.

The term "separator" as used herein means a process unit in which separation of vapour and liquid streams can occur. Thus, at least initially, the first stream is recovered in vapour (gas) form from the separator, whilst the second stream is recovered in liquid form. Examples of "separators" include vapour/liquid separation vessels and fractionation columns. In a vapour/liquid separation vessel a mixture of vapour and liquid is separated by allowing a liquid phase to form in the base of the vessel with a vapour phase above. The liquid phase can then be readily withdrawn from the base, and the vapour overhead. This may be considered as a "single stage" separation vessel in that the vessel may be considered to comprise just one contacting stage. In a fractionation column, in contrast, multiple stages are provided in which vapour passing upwards contacts condensing liquid flowing downwards, such that the vapour becomes enriched in more volatile components and the liquid becomes enriched in the heavier components.

Preferably, the separator is not a fractionation column, and more preferably is a single stage separation vessel, and most preferably a vapour/liquid separation vessel. In particular, the advantages detailed further herein are reduced when a fractionation column is used rather than a vapour/liquid or other single stage separation vessel.

The "separator" may also be considered as a "lights separator", by which as used herein is meant a separator which is operated to provide a separation of "lights" other than monomer, such as hydrogen, nitrogen and methane, from monomer and heavier components. As used herein "lights" means propane and molecules having a molecular weight less than propane. The general concept of "lights separators" for separation of light components in polymerisation processes is well-known (along with "heavies separators" for separation of "heavy" components). One example of such a system is taught by U.S. Pat. No. 6,292,191 although in this document the lights column is operated to remove hydrogen, oxygen, nitrogen and ethylene from diluent to give a purified, olefin-free, diluent stream, whereas in the present invention lights other than ethylene, such as hydrogen, nitrogen and methane, are separated from ethylene (and heavier compounds).

In the separator in the present invention the majority of the fresh feed and the majority of the second component (monomer) are recovered in the second stream and the majority of the first component in the first stream. The process of the present invention results in an improved separation of the first component from the second component (monomer).

The present invention may be applied to a gas phase polymerisation reactor/process. In a gas phase polymerisation process the fresh inert hydrocarbon may be a component which is utilised as a condensable liquid in the process. Such components are added to the reactor in liquid form, and vaporise therein, removing heat of reaction. Preferred examples of such components are butanes, pentanes and hexanes, and preferably pentanes and hexanes.

In a slurry polymerisation process the fresh inert hydrocarbon may be a component which is utilised as a diluent in the process. Such components are added to the reactor and form part of the liquid medium of the slurry in the reactor. Preferred examples of such components for use as diluents are butanes, especially iso-butane, pentanes, hexanes and mixtures thereof. Iso-butane is most preferred.

The process stream in the present invention is preferably a low pressure process stream, by which is meant a process stream which is at a pressure of less than 0.5 MPa (5 bar) even prior to the separator, preferably at a pressure of 0.4 MPa (4 bar) or less. The low pressure process stream is preferably a stream which arises from the low pressure recovery system of the polymerisation process, as described further below.

It will be apparent that the fresh feed to be fed will be or will comprise a component which may, and generally will, already be present in the process stream. Thus, where the fresh feed is an inert hydrocarbon the corresponding inert hydrocarbon will generally also be present in the process stream. Similarly, where the fresh feed is a comonomer, the corresponding comonomer will generally also be present in the process stream.

Preferably the present invention is applied to a slurry phase polymerisation process/reactor. In a slurry process, the fresh inert hydrocarbon preferably is iso-butane.

The fresh feed is preferably fresh comonomer. More preferably both fresh comonomer and fresh inert hydrocarbon are passed to the separator with the process stream.

In particular, it has surprisingly been found that by passing the fresh feeds to the separator with the process stream an increased concentration of the first component is recovered in the first stream. At the same time, the loss of more desired components, such as ethylene and heavier hydrocarbons is reduced.

For example, and in particular, passing a comonomer such as 1-hexene to the separator has surprisingly been found to increase the concentration of nitrogen recovered in the first stream, whilst reducing the amount of isobutane (inert hydrocarbon diluent) and ethylene (monomer) in said stream. Since at least a portion of the first stream is usually disposed of, for example by flare, the reduction in isobutane and ethylene in the first stream results in a reduced loss of said components.

The separator in the first aspect of the present invention is operated at a pressure of 0.4 MPa (4 bar) or less. As noted above the process stream is preferably a stream which arises from the low pressure recovery system of the polymerisation process. Similarly, it is preferred that the separator is itself part of the low pressure recovery system of the polymerisation process as is described further below.

In terms of temperature, the separator may be at any temperature which, in combination with the pressure, produces a first stream comprising the majority of the first component and a second stream comprising the majority of the fresh feed and the majority of the second component. The separator is preferably at a temperature of less than 0° C., for example less than −10° C., and most preferably less than −20° C., for example less than −30° C. In the first aspect of the present invention the pressure is 0.4 MPa (4 bar) or less, preferably 0.3 MPa (3 bar) or less, and most preferably 0.2 MPa (2 bar) or less.

However, in further aspects of the present invention it has been found that where comonomer is present as either a fresh feed and/or in the process stream, the present invention can also be applied even at pressures in the separator of more than 0.4 MPa (4 bar).

Thus, in a second aspect, the present invention provides a process for the introduction of fresh comonomer to a polymerisation reactor, which process comprises passing said fresh comonomer and a process stream comprising a first component selected from hydrogen, nitrogen and methane and a second component which is a monomer to a separator to produce a first stream comprising the majority of the first component and a second stream comprising the majority of the fresh comonomer and the majority of the second component, and passing the second stream to the polymerisation reactor.

Further, in a third aspect, the present invention provides a process for the introduction of fresh inert hydrocarbon to a polymerisation reactor, which process comprises passing said fresh inert hydrocarbon and a process stream comprising a first component selected from hydrogen, nitrogen and methane, a second component which is a monomer and a third component which is a comonomer to a separator to produce a first stream comprising the majority of the first component and a second stream comprising the majority of the fresh inert hydrocarbon, the majority of the second component and the majority of the third component, and passing the second stream to the polymerisation reactor.

It should be noted that, although the second and third aspects may be operated at a pressure above 0.4 MPa (4 bar), pressures of 0.4 MPa (4 bar) or less are still preferred in these aspects.

In particular, the separator is preferably part of a low pressure recovery system of the polymerisation process as described for the first aspect and as detailed further below.

In any of the first to third aspects, as already noted above for the first aspect, the "separator" may be considered as a "lights separator". In general, light components such as hydrogen, methane and nitrogen separate with very high specificity into the first stream, and in particular at least 90% of each of such components fed to the separator are recovered in the first stream. As a particular example, the first stream typically comprises essentially all, by which is meant over 99%, of the hydrogen and nitrogen fed to the separator.

Similarly, heavy components, such as 1-hexene and hexane separate with very high specificity into the second stream, again by which is meant greater than 90% of each of such components fed to the separator are recovered in the second stream. In fact, where the fresh liquid is 1-hexene (comonomer) typically over 99% of 1-hexene fed to the separator is recovered in the second stream.

Intermediate components, such as ethylene, ethane, propane and isobutane tend to pass into both streams in more similar amounts.

A yet further advantage of the present invention is that a proportion of undesired components which may be present in the fresh feeds can be separated therefrom in the first process stream, and thereby at least a portion of these are passed to flare without ever entering the polymerisation reactor. This can apply, for example, to ethane and propane impurities in iso-butane feeds. The effect of this is that feeds with increased amounts of such materials may be used as feedstreams with no or reduced detriment to the polymerisation process.

Another advantage of the present invention is therefore that either less highly specified feeds may be used, or pre-treatment of such streams prior to use may be reduced.

Although it is possible to also feed fresh comonomer and/or fresh inert hydrocarbon feeds directly to the polymerisation reactor, it is preferred that the majority of fresh comonomer passed to the reactor is passed via the claimed process and/or that the majority of fresh diluent passed to the reactor is passed via the claimed process.

More preferably, it is preferred that all of the fresh comonomer passed to the reactor is passed via the claimed process. Most preferably all of the fresh comonomer passed to the reactor is passed via the claimed process and all of the fresh inert hydrocarbon passed to the reactor is passed via the claimed process.

It should be noted that in the preferred process where the reactor is part of a slurry polymerisation process, the process stream typically also comprises significant quantities of diluent liquid. Generally, over 90% of the total isobutane fed to the separator is recovered in the second stream. In fact, the amount of diluent liquid in the low pressure process stream usually exceeds, often substantially, the amount of fresh diluent it is necessary to feed to the system to replace that lost.

In particular, averaged over time, the amount of fresh diluent is usually less than 5% of the total diluent feed to the separator. Further, although some fresh isobutane fed to the separator will be removed in the first vapour stream, not all of this stream is passed to flare. In fact, the make-up fresh diluent rate, which is also equal to the diluent loss rate from the polymerisation process, can be maintained the same in the process of the present invention as a polymerisation process where the fresh inert hydrocarbon (diluent) is not introduced into this separator as claimed.

The fresh feeds can be fed continuously to the separator, or may be fed intermittently. For example, due to the low make-up rates required for fresh diluent it is generally preferred to feed fresh diluent intermittently.

As noted above, another surprising advantage of the present invention is that by passing the fresh feeds to the separator impurities present in these feeds can also be removed i.e. the separator also provides some treatment of the fresh liquid feeds. The impurities can depend on the particular liquid feed, but for iso-butane, for example, can include lighter alkanes, such as propane, which whilst not directly detrimental can otherwise build-up in the process.

Nevertheless, some pre-treatment is still preferred.

Thus, in a fourth aspect, the present invention provides a process for the treatment of a fresh feed stream to be introduced into a polymerisation reactor, said process comprising
   a) Passing the fresh feed stream to a first treatment step where it is treated to remove one or more impurities, and
   b) Passing the fresh feed stream exiting the first treatment step with a process stream comprising a first component selected from hydrogen, nitrogen and methane and a second component which is a monomer to a second treatment step, which is a separator, to produce a first stream comprising the majority of the first component and a second stream comprising the majority of the fresh feed and the majority of the second component, and
   c) Passing the second stream to the polymerisation reactor.

The fresh feed preferably comprises inert hydrocarbon or comonomer.

Where the fresh liquid stream comprises inert hydrocarbon the first treatment step may remove one or more of water and other oxygenated compounds, such as alcohols, MTBE and carbonyl compounds.

Where the fresh liquid stream comprises comonomer the first treatment step may remove one or more of water, MTBE, carbonyl compounds, chloride compounds, sulphur compounds, carbon monoxide and carbon dioxide.

The polymerisation reactor in this fourth aspect is preferably a slurry loop polymerisation reactor to which inert hydrocarbon is fed as a diluent.

Where it is desired to feed both fresh inert hydrocarbon and fresh comonomer, the fresh diluent and fresh comonomer may initially be separately treated in separate treatment steps in step (a), and then combined before passage to the separator.

Alternatively, the fresh inert hydrocarbon and fresh comonomer may be combined and treated in the same treatment step in step (a).

More generally, the processes of the first to fourth aspects of the present invention may each be preferably applied to the provision of fresh feeds to a polymerisation process comprising high and low pressure recovery systems. In particular, said polymerisation process may comprise the steps of:
   1) Polymerising a monomer and a comonomer in a polymerisation reactor, 2) Withdrawing an effluent stream comprising solid polymer and a mixture comprising unreacted monomer and unreacted comonomer, and passing the effluent to a high pressure recovery system comprising
   a. a high pressure separation step for separating a vapour comprising unreacted monomer and unreacted comonomer from said solids, and
   b. a recycle system for recycling at least a portion of the vapour to the polymerisation reactor,
3) Passing the solids from the high pressure recovery system to a low pressure recovery system comprising
   a. a low pressure separation step for separating further unreacted monomer and unreacted comonomer from said solids, and
   b. a recycle system comprising a vapour/liquid separator for recycling at least a portion of the unreacted monomer and unreacted comonomer.

The polymerisation process is preferably a slurry polymerisation process, in which the polymerisation process may comprise the steps of:
1) Polymerising a monomer and a comonomer in the presence of a diluent in a polymerisation reactor,
2) Withdrawing an effluent stream comprising solid polymer and a mixture comprising diluent, unreacted monomer and unreacted comonomer, and passing the effluent to a high pressure recovery system comprising
   a. a high pressure separation step for separating a vapour comprising diluent, unreacted monomer and unreacted comonomer from said solids, and
   b. a recycle system for recycling at least a portion of the vapour to the polymerisation reactor,
3) Passing the solids from the high pressure recovery system to a low pressure recovery system comprising
   a. a low pressure separation step for separating further diluent, unreacted monomer and unreacted comonomer from said solids, and
   b. a recycle system comprising a vapour/liquid separator for recycling at least a portion of the further diluent, unreacted monomer and unreacted comonomer.

As an example in a slurry polymerisation process, high pressure recovery systems are known and widely operated to enable a majority of the diluent, monomer and comonomer to be vaporised and separated from the polymer solids at relatively high pressure, such that the vapour can be condensed without compression for recycle to the reactor. The separated polymer solids are then passed to a low pressure system for recovery of remaining diluent, monomer and comonomer. A low pressure recovery system, in contrast to the high pressure recovery system, generally leads to recovered components, such as diluent, monomer and comonomer, which must be compressed (or further cooled) in order to be able to condense them prior to recycle to the reactor.

("Compression" refers to a process of increasing the pressure ("compressing") a vapour. This is a relatively energy intensive process. Once in the form of liquids, liquids can be pumped to increased pressure with relatively less difficulty. Avoiding "compression", for example by condensing without compression, is highly desirable.)

Examples of such systems can be found, for example, in WO 2005/003188 which discloses the use of a higher pressure flash stage followed by a lower pressure flush stage. However, processes are also known where the lower pressure stage is a flash stage rather than a flush stage, or where both flashing and flushing occur in a single stage. (It can be noted that a flush stage can also be referred to as a "purge stage". The term "flush" is used herein for such steps to avoid any confusion with process purges, which are steps whereby streams are removed from a polymerisation process, for example to flare. The term "purge" as used herein therefore refers to a stream which is removed from the process rather than a flush step.)

The terms "high pressure" and "low pressure" are used herein principally to indicate the relative pressures of the two recovery systems.

Generally, however, "high pressure" as used herein generally refers to streams and stages which are at a pressure of 0.5 MPa (5 bar) and above, and usually 0.7 MPa (7 bar) and above, and "low pressure" generally refers to streams and stages which are at a pressure of less than 0.5 MPa (5 bar), usually less than 0.4 MPa (4 bar).

The high and low pressure separation steps in such systems above are typically vapour/solids separation steps, such as flash vessels and flush vessels.

The separator to which the fresh feed is passed according to the first to fourth aspects of the present invention is preferably the "vapour/liquid separator" in the low pressure recovery system of such a process.

In a most preferred embodiment as applied to such a polymerisation process, a portion of the vapour recovered in step 2(a) is condensed, let-down in pressure, and also passed to the vapour/liquid separator.

In general, this would be expect to be disadvantageous because any recovered streams let-down in pressure have to be recompressed to be re-used. To avoid the requirement for this as much as possible is exactly the reason why high pressure separation systems are used to try to maximise high pressure recovery of reaction components.

Surprisingly, however, it has been found that passing a portion of the vapour recovered at high pressure to the vapour/liquid separator (after condensing and deliberately letting down the pressure) results in yet further enhancement in the separations process, and in particular, in an overall reduction in desired components lost to flares.

Further, where the separator is operated at a pressure of less than 0.4 MPa (4 bar) and at a temperature of less than −10° C. (i.e. as a low pressure and low temperature separator) a yet further advantage may be obtained because at such low temperatures condensation of the components as the second stream can occur at relatively low pressures compared to low pressure streams at relatively higher temperatures. Thus, only a relatively small pressure increase is required to obtain condensation of the stream. This allows the use of devices which need only provide a relatively small pressure increase, by which is meant a maximum of 5 bar. Any device or assembly of devices arranged in series or in parallel may be used which increase the pressure of a gas or a mixture of gases by a maximum 5 bar, and preferably by a maximum 3 bar. Examples of such devices include blowers (such as positive displacement blowers) and screw compressors. Such devices are generally cheaper and simpler to operate than devices which can provide higher pressure increases, such as reciprocating or labyrinth compressors. The condensed stream once formed can then be pumped to reaction pressure without a requirement for compression. In the fourth aspect, the portion of the vapour recovered in step 2(a) may be passed directly to the vapour/liquid separator or may be passed to the earlier treatment step with the fresh feed.

The process of the first to fourth aspects of the present invention may also be advantageously applied to a polymerisation process operating in two or more reactors. The operation of two loop reactors in series, for example, is well-known.

In particular, the fresh feed may be passed to a separator as claimed in any of the first to further aspects to produce a second stream, and a first portion of said second stream is passed to a first of said at least 2 reactors and a second portion of said second stream is passed to a second of said at least 2 reactors.

It is preferred that no further fresh feeds of fresh diluent or fresh comonomer are passed to the first reactor or no further fresh feeds of fresh diluent or fresh comonomer are passed to the second reactor. Most preferably no further fresh feeds of fresh diluent or fresh comonomer are passed to the first reactor and no further fresh feeds of fresh diluent or fresh comonomer are passed to the second reactor.

As noted above, the present invention generally provides improved separation of the first component from the second component (monomer).

Thus, in further aspects, the present invention provides a process for improving the separation of a first component selected from hydrogen, nitrogen and methane from a second component which is a monomer by passing a process stream comprising said first and second components to a separator, said improvement comprising one or more of the following:
1) also passing to the separator fresh comonomer,
2) also passing to the separator at least one fresh feed selected from fresh comonomer and fresh inert hydrocarbon whilst operating the separator at a pressure of 0.4 MPa or less, and
3) also passing to the separator fresh inert hydrocarbon where said process stream also comprises a third component which is a comonomer.

The first component is preferably nitrogen.

The preferred features are generally as described for the first to fourth aspects above.

The present invention allows to obtain a polymerisation process which has a high efficiency for desired components of the final polymer, such as monomer, but "low" efficiency for other components (such as impurities).

As used herein, "efficiency" is a measure of the amount of a particular material which is fed and which is not purged. For example, monomer efficiency is the amount of monomer fed which is not purged.

The monomer efficiency is a measure of the amount of the monomer which ends up in the polymer product, and is determined from the amount of fresh monomer fed to a process and the amount of monomer which is purged. The monomer purge rate may be determined from the purge flow and the concentration of monomer in the purge stream, which can be measured by GC, for each purge stream present. The efficiency may be determined instantaneously, based on flow rate measurements at a particular time, but preferably is determined over a period of time, for example based on averaged instantaneous measurements or on total amounts fed and purged determined over a period of at least several hours, as this generally gives a more accurate measurement. The monomer efficiency is determined by subtracting the amount purged from the amount fed, and then dividing the result by the amount fed. This answer is multiplied by 100 to give the efficiency as a percentage.

The process of the present invention is able to provide a monomer efficiency in excess of 99.5%, for example of 99.6% and above, and most preferably of 99.7% and above.

It is worth noting that, whilst monomer efficiencies of polymerisation processes are generally very high (above 99%), at the scale of commercial polymerisation processes even what appear as relatively minor increases in efficiency can result in significant cost savings, as well as significant reductions in hydrocarbon emissions or combustion products from hydrocarbon emissions (when flared). For example, in a process producing 50 tonnes/hour of polymer, an increase in monomer efficiency by only 0.1% is still a reduction in monomer losses of 50 kg/hour.

In contrast to a high monomer efficiency, it has been found that a low hydrogen efficiency of a polymerisation process can be advantageous. In particular, hydrogen is more cost effectively flared than recycled and recovered to the overall polymerisation process. An advantage of relatively low hydrogen efficiencies is that other impurities which can be present in fresh hydrogen feeds, such as methane and CO, are also efficiently purged from the system via the purge streams, and purification of fresh hydrogen feed via PSA can be avoided.

The present invention can result in a polymerisation process which preferably has a hydrogen efficiency, measured of the amount of the fed hydrogen which is not purged of 80% or less, preferably of 70% or less, and most preferably of 60% or less.

The hydrogen efficiency may be determined in a similar manner to the monomer efficiency, and in particular by determining the amount of hydrogen purged from the purge flow and the hydrogen concentration in the purge stream, which can be measured by GC, for each purge stream present and comparing this to the amount of hydrogen fed to the process.

The present invention will now be illustrated by reference to the following examples.

EXAMPLES

Comparative Example

Ethylene is polymerised in two slurry loop reactors in series to produce a monomodal polyethylene with a density of 939 kg/m$^3$ and a melt index MI5 of 0.35 g/10 min. The total production rate is 45 tonnes/hour.

In the first reactor ethylene is polymerised with 1-hexene using a chromium-based catalyst system, in the presence of hydrogen and with isobutane as diluent. Polymer from the first reactor is passed to a second reactor wherein further ethylene is polymerised in the presence of 1-hexene as comonomer, again in the presence of hydrogen and isobutane.

Polymer slurry is withdrawn from the first reactor and directly passed to the second reactor.

Polymer slurry is withdrawn from the second reactor and passed via a slurry heater, in which the liquid components of the slurry are vaporised to a separating tank at a pressure of 1.0 MPa.

The vapour from the separating tank overhead is further treated, condensed and recycled to the reactors via a high pressure recovery system.

Polymer solids are withdrawn from the separating tank for further processing in a flush vessel at a pressure of 0.04 MPa. The flushing takes place by contact in two vertically orientated stages with polymer being introduced at the top and withdrawn from the base of the vessel, and with a recycled flush gas being introduced into the upper stage and nitrogen being introduced into the lower stage.

A mixture of the flush gases and recovered diluent/monomer is recovered from the top of the flush vessel.

The stream is pressurised, combined with a recycle from a heavies separation unit, cooled and the mixture passed to a separator at a pressure of 0.3 MPa and at a temperature of −20° C.

The total flow to the separator is approximately 9300 kg/hr and comprises isobutane, 1-hexene, nitrogen, ethane, ethylene, propane, hexane, methane and hydrogen. From the base of the separator is recovered a stream at a flow rate of approximately 7243 kg/hr.

The base stream comprises 99.6% of the 1-hexene and hexane fed to the separator, as well as 91% of the isobutane.

The base stream is recycled, after compression, to the polymerisation process.

Overhead from the separator is recovered a stream at a flow rate of 2057 kg/hr comprising nitrogen, isobutane, ethane, ethylene and propane with smaller amounts of 1-hexene, hexane, methane and hydrogen.

The overhead stream comprises 93.9% of the methane, 98.4% of the nitrogen and 99.6% of the hydrogen fed to the separator, as well as 71.9% of the ethane.

The majority of this stream is recycled to the flush vessel. The remainder of this stream is passed to a flare, 564 kg/hr of nitrogen is flared, along with 105 kg/h of ethylene, 316 kg/h of isobutane, 6.5 kg/hr of propane, 1.96 kg/hr of methane, 0.86 kg/hr of 1-hexene and 1.18 kg/hr of hydrogen.

In this comparative example the fresh 1-hexene is fed directly to the reactors and the fresh isobutane in the high pressure recovery system.

Example 1

The Comparative Example is repeated except that the stream passed to the separator is, prior to the cooling step, mixed with 1820 kg/hr of fresh 1-hexene (99% 1-hexene, 1% hexane).

The total flow to the separator is approximately 11117 kg/hr.

From the base of the separator is recovered a stream at a flow rate of approximately 9136 kg/hr.

The base stream comprises 99.7% of the 1-hexene and hexane fed to the separator, as well as 92.4% of the isobutane.

The base stream is recycled, after compression, to the polymerisation process. Overhead from the separator is recovered a stream at a flow rate of 1981 kg/hr.

The overhead stream comprises 92.9% of the methane, 98.1% of the nitrogen and 99.4% of the hydrogen fed to the separator, as well as 55.7% of the ethane.

The majority of this stream is recycled to the flush vessel. The remainder of this stream is passed to a flare. 560 kg/hr of nitrogen is flared, along with 95 kg/h of ethylene, 254 kg/h of isobutane, 5.2 kg/hr of propane, 1.90 kg/hr of methane, 3.4 kg/hr of 1-hexene and 1.18 kg/hr of hydrogen By comparison to the Comparative Example it can be seen that, by passing the fresh 1-hexene feed to the low pressure system, the losses of ethylene and isobutane in the flare are reduced. In particular, the addition of 1-hexene reduces the losses of isobutane by approximately 62 kg/hr, or 20%, and the losses of ethylene by approximately 10 kg/hr, or 10%, compared to the Comparative Example.

Example 2

The Comparative Example is repeated except that the stream passed to the separator is, prior to the cooling step, mixed with 360 kg/hr of fresh isobutane (97% isobutane, 3% propane).

The total flow to the separator is approximately 9660 kg/hr.

From the base of the separator is recovered a stream at a flow rate of approximately 7607 kg/hr.

The base stream comprises 99.6% of the 1-hexene and hexane fed to the separator, as well as 91.4% of the isobutane.

The base stream is recycled, after compression, to the polymerisation process.

Overhead from the separator is recovered a stream at a flow rate of 2053 kg/hr. The overhead stream comprises 93.4% of the methane, 98.4% of the nitrogen and 99.5% of the hydrogen fed to the separator, as well as 58.6% of the ethane.

The majority of this stream is recycled to the flush vessel. The remainder of this stream is passed to a flare. 564 kg/hr of nitrogen is flared, along with 102 kg/h of ethylene, 316 kg/h of isobutane, 6.6 kg/hr of propane, 1.95 kg/hr of methane, 0.82 kg/hr of 1-hexene and 1.18 kg/hr of hydrogen Compared to the Comparative Example, the purge rates of the various components are essentially the same. However by passing fresh isobutane directly in the low pressure system in this Example, rather than directly to the reactors, as in the Comparative Example, the amount of ethylene purged is slightly reduced and the amount of propane purge is increased. Although the propane purge increase is small it has a significant impact on the propane amount in the reactor as propane is an inert and accumulates. In the Comparative Example, the polymer slurry withdrawn from the second reactor comprises approximately 519 kg/hr of propane, but in Example 2 this is reduced to approximately 475 kg/hr, reflecting a reduction in the amount of propane inert passed to the reactors.

Example 3

The Comparative Example is repeated except that the stream passed to the separator is, prior to the cooling step, mixed with 1830 kg/hr of fresh 1-hexene (99% 1-hexene, 1% hexane) and 300 kg/hr of fresh isobutane (97% isobutane, 3% propane).

The total flow to the separator is approximately 11426 kg/hr.

From the base of the separator is recovered a stream at a flow rate of approximately 9447 kg/hr.

The base stream comprises 99.7% of the 1-hexene and hexane fed to the separator, as well as 92.7% of the isobutane.

The base stream is recycled, after compression, to the polymerisation process. Overhead from the separator is recovered a stream at a flow rate of 1979 kg/hr.

The overhead stream comprises 92.4% of the methane, 98.1% of the nitrogen and 99.4% of the hydrogen fed to the separator, as well as 54.8% of the ethane.

The majority of this stream is recycled to the flush vessel. The remainder of this stream is passed to a flare. 560 kg/hr of nitrogen is flared, along with 93 kg/h of ethylene, 255 kg/h of isobutane, 5.3 kg/hr of propane, 1.89 kg/hr of methane, 3.3 kg/hr of 1-hexene and 1.17 kg/hr of hydrogen As with Example 1, by comparison to the Comparative Example it can be seen that the losses of ethylene and isobutane in the flare are reduced. The reductions are similar to those seen in Example 1.

Compared to Example 1, the purge rates of the various components are similar. However by passing fresh isobutane directly to the low pressure system in this Example, rather than directly to the reactors, as in the Comparative Example, the amount of propane purge is increased.

As in Example 2 the increase in propane purge is small but has a significant impact on the propane level in the reactors as propane is an accumulating inert.

The comparative example had approximately 519 kg/h of propane coming out of the second reactor, and this amount was reduced in example 1 to approximately 500 kg/h. This amount is reduced to 466 kg/h in this example, again showing the benefit of passing the fresh isobutane to the low pressure system instead of sending it to the high pressure recovery system (or directly to the reactors).

The invention claimed is:

1. A process for the introduction of a fresh feed selected from fresh comonomer and fresh inert hydrocarbon to a polymerisation reactor wherein the polymerisation reactor is part of a polymerisation process comprising high and low pressure recovery systems, said high pressure recovery system being at a pressure of 0.5 MPa (5 bar) or above and said low pressure recovery system being at a pressure of less than 0.5 MPa (5 bar), which process comprises passing said fresh feed and a process stream comprising a first component selected from hydrogen, nitrogen and methane and a second component which is a monomer to a separator which is part of the low pressure recovery system and is at a pressure of 0.4 MPa or less to produce a first stream comprising the majority of the first component and a second stream comprising the majority of the fresh feed and the majority of the second component, and passing the second stream to the polymerisation reactor.

2. A process according to claim 1 where the fresh feed is fresh comonomer.

3. A process according to claim 1 where the separator is a single stage separation vessel.

4. A process according to claim 1 wherein the polymerisation reactor is a slurry phase reactor and the fresh inert hydrocarbon is a component which is utilised as a diluent in the process.

5. A process according to claim 1 wherein both fresh comonomer and fresh inert hydrocarbon are passed to the separator with the process stream.

6. A process according to claim 1 where the separator is at a temperature of less than 0° C. and/or where the separator is at a pressure of 0.3 MPa or less.

7. A process according to claim 1 wherein the majority of fresh comonomer passed to the reactor is passed via the claimed process and/or that the majority of fresh inert hydrocarbon passed to the reactor is passed via the claimed process.

8. A process for the treatment of a fresh feed stream to be introduced into a polymerisation reactor, said process comprising
  a) Passing the fresh feed stream to a first treatment step where it is treated to remove one or more impurities, and
  b) Passing the fresh feed stream exiting the first treatment step with a process stream comprising a first component selected from hydrogen, nitrogen and methane and a second component which is a monomer to a second treatment step which is a separator to produce a first stream comprising the majority of the first component and a second stream comprising the majority of the fresh feed and the majority of the second component, and
  c) Passing the second stream to the polymerisation reactor.

9. A process according to claim 8 wherein the fresh feed comprises inert hydrocarbon or comonomer.

10. A process according to claim 8 wherein the polymerisation reactor is a slurry loop polymerisation reactor to which inert hydrocarbon is fed as a diluent.

11. A process according to claim 8 for wherein the polymerisation reactor is part of a polymerisation process comprising high and low pressure recovery systems, said high pressure recovery system being at a pressure of 0.5 MPa (5 bar) or above and said low pressure recovery system being at a pressure of less than 0.5 MPa (5 bar), the separator being part of the low pressure recovery system and being at a pressure of 0.4 MPa or less.

12. A process according to claim 11 where the separator is at a temperature of less than 0° C. and/or where the separator is at a pressure of 0.3 MPa or less.

13. A process according to claim 1 wherein the polymerisation process comprises the steps of:
  1) Polymerising a monomer and a comonomer in a polymerisation reactor,
  2) Withdrawing an effluent stream comprising solid polymer and a mixture comprising unreacted monomer and unreacted comonomer, and passing the effluent to a high pressure recovery system comprising
    a. a high pressure separation step for separating a vapour comprising unreacted monomer and unreacted comonomer from said solids, and
    b. a recycle system for recycling at least a portion of the vapour to the polymerisation reactor,
  3) Passing the solids from the high pressure recovery system to a low pressure recovery system comprising
    a. a low pressure separation step for separating further unreacted monomer and unreacted comonomer from said solids, and
    b. a recycle system comprising a vapour/liquid separator for recycling at least a portion of the unreacted monomer and unreacted comonomer,
  said separator to which the fresh feed is passed being the "vapour/liquid separator" of step 3(b).

14. A process according to claim 13 wherein a portion of the vapour recovered in step 2(a) is condensed, let-down in pressure, and also passed to the vapour/liquid separator of step 3(b).

15. A process according to claim 11 wherein the polymerisation process comprises the steps of:
  1) Polymerising a monomer and a comonomer in a polymerisation reactor,
  2) Withdrawing an effluent stream comprising solid polymer and a mixture comprising unreacted monomer and unreacted comonomer, and passing the effluent to a high pressure recovery system comprising
    a. a high pressure separation step for separating a vapour comprising unreacted monomer and unreacted comonomer from said solids, and
    b. a recycle system for recycling at least a portion of the vapour to the polymerisation reactor,
  3) Passing the solids from the high pressure recovery system to a low pressure recovery system comprising
    a. a low pressure separation step for separating further unreacted monomer and unreacted comonomer from said solids, and
    b. a recycle system comprising a vapour/liquid separator for recycling at least a portion of the unreacted monomer and unreacted comonomer,
  said separator to which the fresh feed is passed being the "vapour/liquid separator" of step 3(b).

16. A process according to claim 15 wherein a portion of the vapour recovered in step 2(a) is condensed, let-down in pressure, and also passed to the vapour/liquid separator of step 3(b).

17. A process according to claim 6 where the separator is at a temperature of less than −20° C. and/or where the separator is at a pressure of 0.2 MPa or less.

18. A process according to claim 7 wherein all of the fresh comonomer passed to the reactor is passed via the claimed process.

19. A process according to claim 12 where the separator is at a temperature of less than −20° C. and/or where the separator is at a pressure of 0.2 MPa or less.

* * * * *